(12) United States Patent
Lawton et al.

(10) Patent No.: US 9,342,320 B2
(45) Date of Patent: May 17, 2016

(54) METHOD FOR FACILITATING COOPERATIVE INTERACTION BETWEEN SOFTWARE APPLICATIONS

(75) Inventors: Kyle Lawton, Manchester, NH (US); Erik Heath, Seymour, CT (US)

(73) Assignee: McKesson Technologies Inc., Alpharetta, GA (US)

( * ) Notice: Subject to any disclaimer, the term of this patent is extended or adjusted under 35 U.S.C. 154(b) by 1657 days.

(21) Appl. No.: 12/122,641

(22) Filed: May 16, 2008

(65) Prior Publication Data

US 2009/0288037 A1    Nov. 19, 2009

(51) Int. Cl.
| | | |
|---|---|---|
| *G06F 3/00* | (2006.01) | |
| *G06F 3/048* | (2013.01) | |
| *G06F 9/44* | (2006.01) | |
| *G06F 3/0481* | (2013.01) | |
| *G06F 19/00* | (2011.01) | |

(52) U.S. Cl.
CPC ............ *G06F 9/4443* (2013.01); *G06F 3/0481* (2013.01); *G06F 19/321* (2013.01); *G06F 19/3425* (2013.01)

(58) Field of Classification Search
USPC ......... 715/700, 733, 748, 751, 764, 769, 770, 715/804, 808, 866
See application file for complete search history.

(56) References Cited

U.S. PATENT DOCUMENTS

| | | | |
|---|---|---|---|
| 4,489,387 A | | 12/1984 | Lamb et al. |
| 5,005,143 A | | 4/1991 | Altschuler et al. |
| 5,157,763 A | * | 10/1992 | Peters et al. .................. 715/769 |
| 5,301,268 A | * | 4/1994 | Takeda .......................... 719/329 |
| 5,404,442 A | * | 4/1995 | Foster et al. .................. 715/769 |
| 5,583,758 A | | 12/1996 | McIlroy et al. |
| 5,606,674 A | * | 2/1997 | Root .............................. 715/769 |
| 5,764,873 A | * | 6/1998 | Magid et al. .................. 715/769 |
| 5,892,511 A | * | 4/1999 | Gelsinger et al. ............. 715/794 |
| 6,011,552 A | * | 1/2000 | Ramanathan et al. ........ 715/803 |
| 6,049,794 A | | 4/2000 | Jacobs et al. |
| 6,061,058 A | * | 5/2000 | Owens et al. ................. 715/769 |
| 6,126,596 A | | 10/2000 | Freedman |
| 6,309,305 B1 | * | 10/2001 | Kraft ............................. 455/566 |
| 6,630,946 B2 | * | 10/2003 | Elliott et al. .................. 715/781 |

(Continued)

OTHER PUBLICATIONS

Special Edition Using Microsoft Office 2003, Feb. 8, 2002, 6 pages.*

(Continued)

*Primary Examiner* — Yongjia Pan
(74) *Attorney, Agent, or Firm* — Alston & Bird LLP

(57) ABSTRACT

A computer software system is disclosed for single step coordination between software applications. A monitoring application automatically identifies a target application and presents a prompting window, such that if possible (but not necessarily) it appears to be attached to a side of the target window. Clicking a control in the prompting window automatically activates a secondary application, and automatically transfers information from the target application to the secondary application. Target desktop windows can be identified by their window captions and target HTML windows by their URL addresses. Controls on prompting windows can activate multiple secondary applications and/or different secondary application modes. Information can be obtained from a target application by reading a file stored for that purpose by the target application, by interprocess communication, or by screen scraping. In one general aspect, a medical test result viewing application is coordinated with a medical test result processing application.

17 Claims, 7 Drawing Sheets

(56) References Cited

U.S. PATENT DOCUMENTS

| | | | |
|---|---|---|---|
| 6,711,564 B2 * | 3/2004 | Crucs | |
| 6,739,877 B2 | 5/2004 | Bailey et al. | |
| 6,915,265 B1 | 7/2005 | Johnson | |
| 7,039,723 B2 | 5/2006 | Hu et al. | |
| 7,072,931 B2 | 7/2006 | Goldhaber et al. | |
| 7,337,409 B2 * | 2/2008 | Doblmayr et al. | 715/769 |
| 7,478,336 B2 * | 1/2009 | Chen et al. | 715/770 |
| 7,516,398 B2 * | 4/2009 | Yang | 715/230 |
| 7,555,723 B1 * | 6/2009 | Coe | 715/769 |
| 7,624,353 B2 * | 11/2009 | Beumer | 715/764 |
| 7,650,575 B2 * | 1/2010 | Cummins et al. | 715/769 |
| 7,676,761 B2 * | 3/2010 | Oliver et al. | 715/803 |
| 7,735,017 B2 * | 6/2010 | Cunningham et al. | 715/770 |
| 7,774,753 B1 * | 8/2010 | Reilly et al. | 717/120 |
| 7,840,967 B1 * | 11/2010 | Czajkowski et al. | 719/312 |
| 7,877,406 B2 * | 1/2011 | Crucs | 707/772 |
| 8,020,101 B2 * | 9/2011 | Kesavarapu | 715/724 |
| 8,255,819 B2 * | 8/2012 | Chang et al. | 715/769 |
| 2003/0187689 A1 | 10/2003 | Barnes et al. | |
| 2004/0015539 A1 * | 1/2004 | Alegria et al. | 709/203 |
| 2004/0070622 A1 * | 4/2004 | Cossey et al. | 345/769 |
| 2004/0210846 A1 * | 10/2004 | Olsen | 715/761 |
| 2005/0097189 A1 * | 5/2005 | Kashi | 709/217 |
| 2006/0075359 A1 * | 4/2006 | Bauchot et al. | 715/790 |
| 2007/0294630 A1 * | 12/2007 | Duncan et al. | 715/764 |
| 2008/0082932 A1 * | 4/2008 | Beumer | 715/770 |
| 2008/0201656 A1 * | 8/2008 | Kim et al. | 715/770 |

OTHER PUBLICATIONS

Bryce Whitty, Automation with AutoIT Tutorial: Part 2, May 7, 2008, 4 pages.*

Window Titles and Text (Advanced), Dec. 25, 2007, 2 pages.* http://www.theabr.org/RO_MOC_PQI.htm Downloaded Jan. 7, 2008 Radiation Oncology General Information about Practice Quality Improvement (PQI) Projects.

http://www.rt-image.com/Commissure_Inc_Radiology_speech_reporting_system/content=9204J05C4856848640769A7244A860441 Downloaded Jan. 7, 2008 Commissure Inc. Radiology speech-reporting system.

* cited by examiner

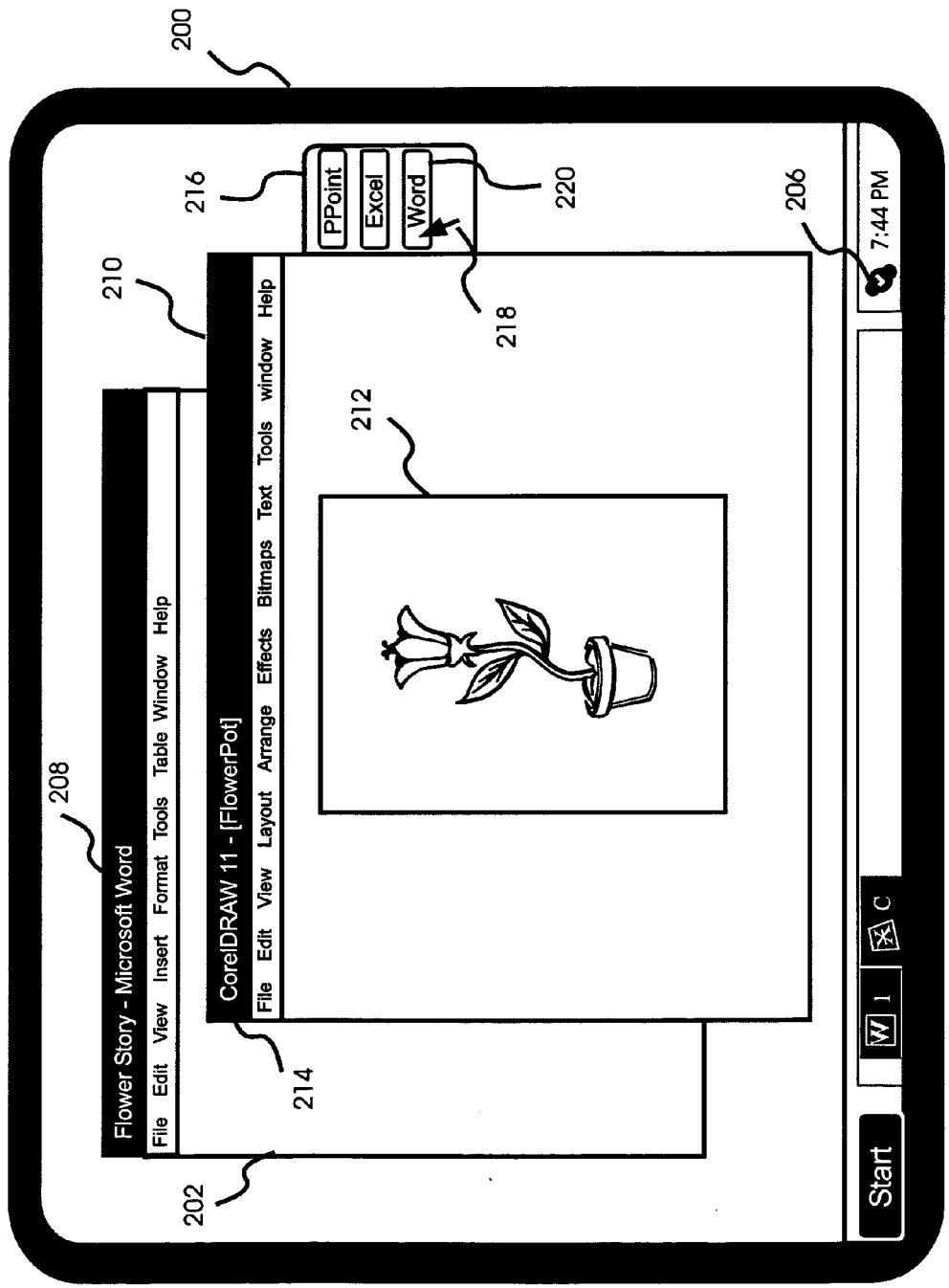

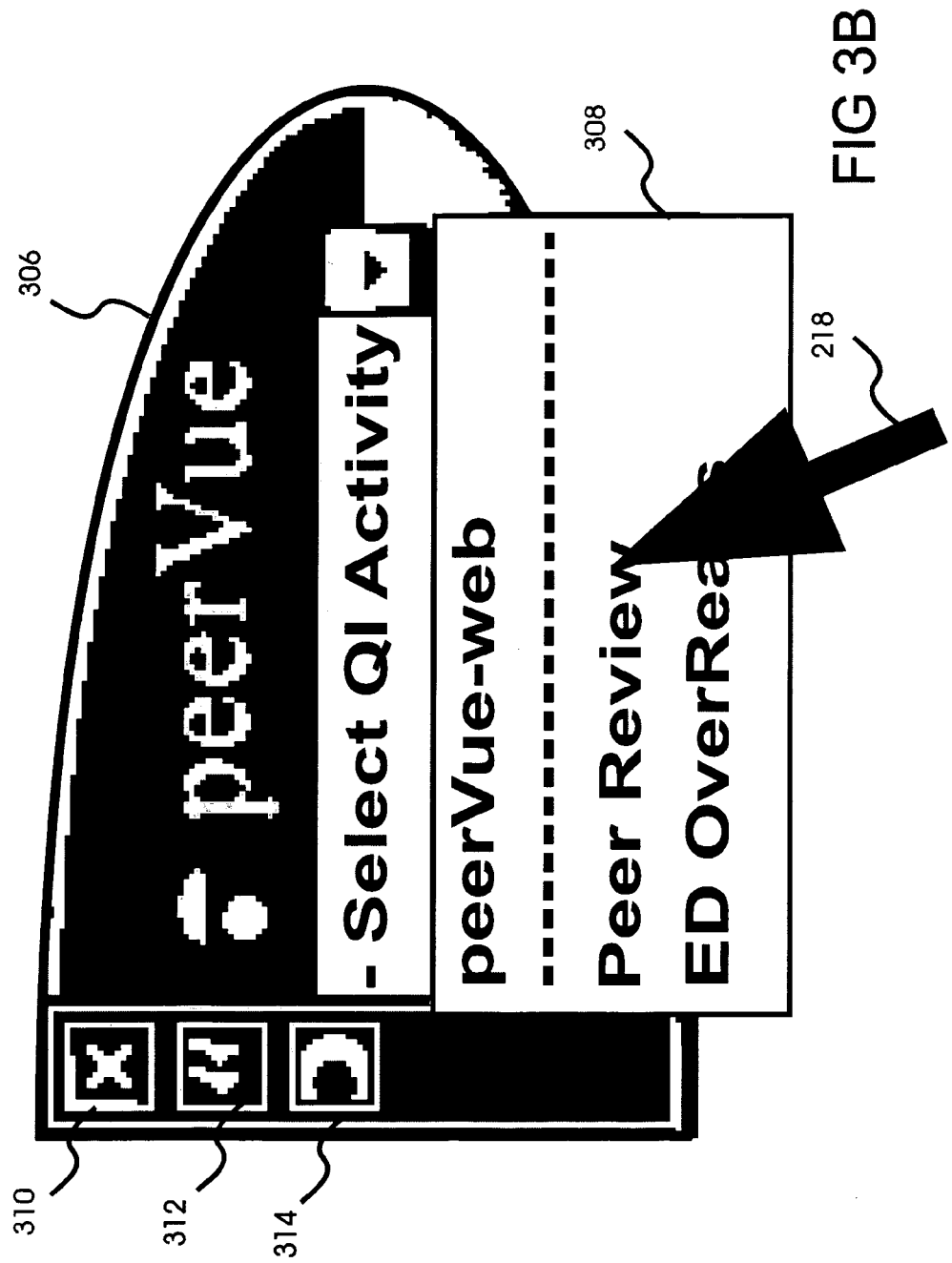

METHOD FOR FACILITATING COOPERATIVE INTERACTION BETWEEN SOFTWARE APPLICATIONS

FIELD OF THE INVENTION

The invention generally relates to communication between software applications, and more specifically to cooperative interaction between software applications.

BACKGROUND OF THE INVENTION

In many computing environments it can be desirable to analyze and manipulate information through the coordinated use of more than one software application. For example, in a business environment it may be desirable to process information using multiple applications from within an "office suite" such as Microsoft Office. A word processing application such as Microsoft Word or a presentation generating application such as Microsoft PowerPoint can be used to prepare a report or a presentation based on numeric results calculated by a spreadsheet application such as Microsoft Excel. Similarly, in a medical environment a radiologist using a PACS application to interpret an MRI study may wish to switch to a separate peer review application so as to record a peer review of another radiologist's interpretation regarding the MRI study.

In general, the coordinated use of multiple software applications to process information requires the steps of suspending a first application, transferring information from the first application to a second application, and initiating and/or switching to the second application.

A number of methods are known for switching control and transferring information between unrelated applications. By far the most common method is "cut and paste," whereby a user selects alphanumeric information from a first application, "cuts" or "copies" it to a temporary storage location, often referred to as the "clipboard," and then "pastes" it into a location within a second application. This approach is almost universal, since it does not require that the two applications have any specific knowledge about each other. However, it is labor intensive and time consuming, since a user must manually take the steps of selecting and copying the information from the first application, initiating and/or switching to the second application, and then pasting the information into the second application.

Many applications intentionally make selected information available to other applications by storing the selected information in a file stored in a well defined location. The file typically has a well defined name and the information is typically stored in a standard format, such as ASCII text (.txt) or XML, that can easily be interpreted by unrelated applications. In such cases, a second, unrelated application can obtain desired information from the first application by simply reading the file stored by the first application. All that is required is that the application receiving the information be aware of the name, formatting, and location of the file containing the information. However, this approach is still labor intensive and time consuming, since it typically remains necessary for a user to manually suspend use of the first application, initiate and/or switch to the second application, and initiate reading by the second application of the information-containing file created by the first application.

Another approach to communicating information between applications is to use standard interprocess communication protocols. A category of interprocess protocols called Component Object Module (COM) protocols includes Object Linking and Embedding (OLE), OLE-Automation, ActiveX, COM+, and DCOM. Other interprocess protocols include Microsoft .NET and various web services provided through the Windows Communication Foundation (WCF). Such protocols can be used either in a direct mode to simply pass information between applications, or in an automated mode whereby one application can be accessed from within another application. For example, by using OLE Automation or Microsoft .NET an image created by a graphical application can under certain circumstances be embedded within a word processing application in such a way that double-clicking on the image within the word processing application automatically switches to and/or initiates the graphical application, and presents the image in the graphical application ready for further graphical manipulation.

When used in a direct mode, transfer of information using interprocess protocols such as COM typically still require manual suspension of the first application, initiating or switching to the second application, and initiation of the information transfer. Using an interprocess protocol in automated mode to imbed one application within another can eliminate the need for these separate, manual steps. However, such automated use of interprocess protocols typically requires an extensive programming effort so as place one application in direct communication with the other. In cases where it is desirable for an application to coordinate with a plurality of other applications, the required programming effort can be prohibitive, since each of the plurality of other applications may support a different interprocess protocol.

SUMMARY OF THE INVENTION

A computer software system is claimed that provides for single step coordination of software applications with only modest programming required. A monitoring application identifies target windows belonging to a target application, and automatically presents a prompting window in a location that is coordinated with the target window, if possible placing the prompting window so that it appears to be "attached" to the target window. Clicking on a control included in the prompting window causes a second application to be automatically initiated and/or activated, and also causes information from the target application to be automatically transferred to the second application.

In a first general aspect of the invention, the computer software system has a set of instructions for controlling a general purpose computer so as to coordinate the activity of two software applications operable on the computer, the software system carrying out a method comprising the following steps: monitoring the computer so as to recognize an activated target window of a target application; upon recognition of an activated target window, displaying a prompting window in a visible location cooperative with the target window, the prompting window including a selectable control; and upon selection of the control, activating a coordinating application, obtaining information from the target application, and providing the information to the coordinating application.

In preferred embodiments, the target window is a windows form displayed within a windows operating environment. And in some of these preferred embodiments, each windows form displayed within the windows operating environment includes an alphanumeric caption, and a target windows form is recognized at least partly by matching at least part of its caption with a target alphanumeric string. In some of these preferred embodiments the captions of all active windows forms are compared at regular intervals with the target alphanumeric string, such as every 500 ms.

In other preferred embodiments, the target window is a URL window displayed by an HTML browsing application.

In various preferred embodiments the prompting window includes a plurality of controls. In some of these embodiments the plurality of controls includes at least two controls that correspond to different software applications, such that the corresponding application is activated when one of the two controls is selected. And in other of these embodiments the plurality of controls includes at least two controls that correspond to different operational modes of the same software application, such that the application is activated in the corresponding operation mode when one of the two controls is selected.

In preferred embodiments the prompting window can be displayed with an edge substantially coincident with an edge of the target window, so as to cause the prompting window to appear to be attached to the target window. In some of these embodiments, the prompting window can be displayed such that it overlaps the target window. And in other of these embodiments the prompting window can be displayed such that it extends beyond the target window. In still other of these embodiments the prompting window can be displayed such that it does not make contact with the target window.

In various embodiments the information is extracted from a file created by the target application. In some of these embodiments the format of the file is one of XML and ASCII text. In other preferred embodiments the information is obtained from the target application through an interprocess communication protocol, such as a COM protocol. And in some preferred embodiments the information is obtained from the target application by extracting it from the target window.

In a second general aspect of the invention, the computer software system has a set of instructions for controlling a general purpose computer so as to coordinate the activity of a medical test result viewing application and a secondary medical test result processing application, the software system carrying out a method comprising the following steps: monitoring the computer so as to recognize activation of a target window of the medical test result viewing application; upon recognition of activation of the target window, displaying a prompting window in a visible location cooperative with the target window, the prompting window including a selectable control; and upon selection of the control activating the secondary medical test result processing application, obtaining information pertaining to a selected test result from the medical test result viewing application, and providing the information to the secondary medical test result processing application.

In preferred embodiments of this general aspect, the prompting window can be displayed with an edge substantially coincident with an edge of the target window, so as to cause the prompting window to appear to be attached to the target window.

BRIEF DESCRIPTION OF THE DRAWINGS

FIG. 2B is an illustration of the computer display of FIG. 2A showing an active graphical illustration windows form with a prompting window attached thereto, and with a cursor pointing to a control on the prompting window that is linked to the word processing windows form;

FIG. 3B is a close-up illustration of the prompting window of FIG. 3A; and

DETAILED DESCRIPTION OF PREFERRED EMBODIMENTS

Figure 1:
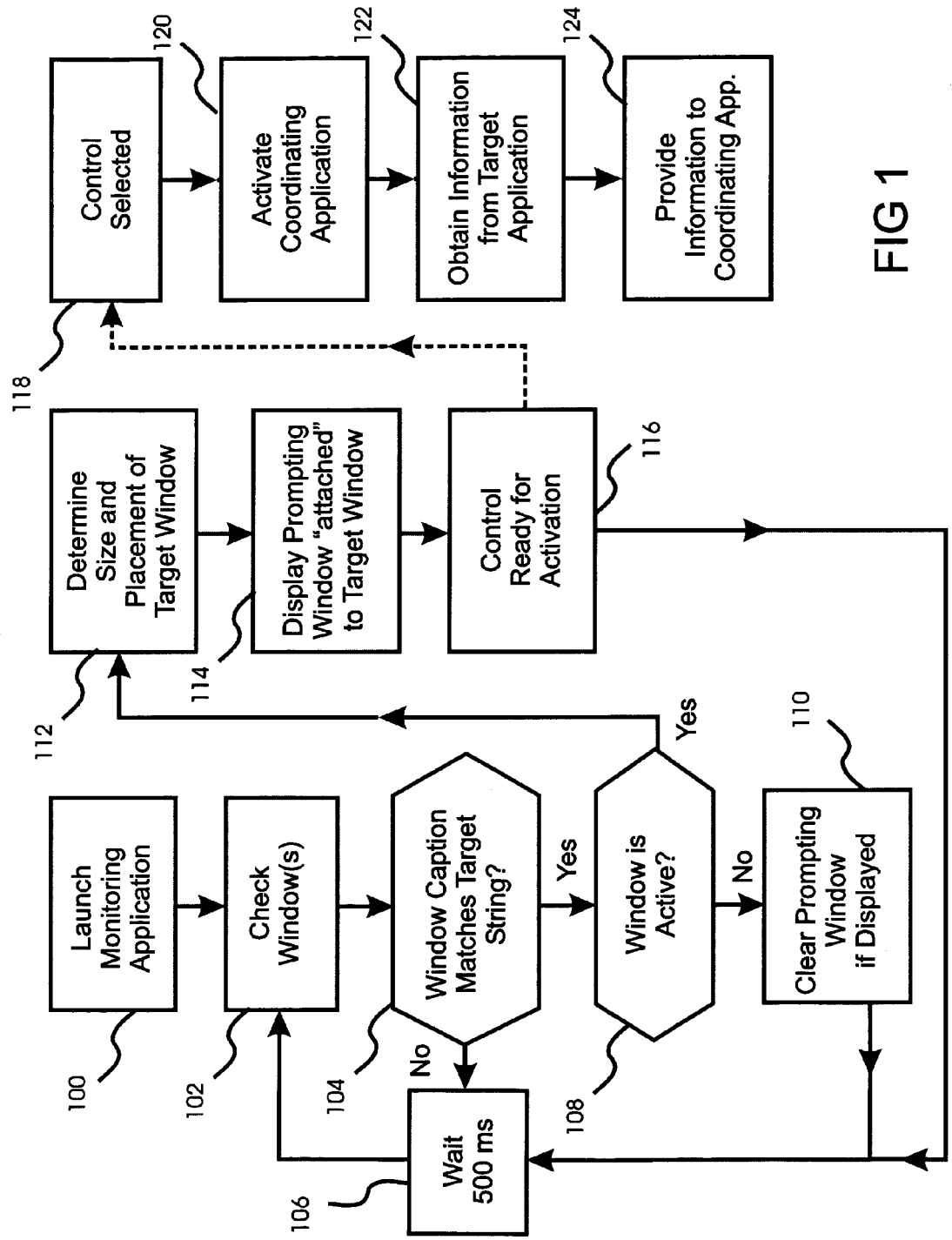
FIG. 1 is a functional diagram of the method carried out by the computer software system of the present invention.

With reference to FIG. 1, the method carried out by the computer software system of the present invention begins with the launch 100 of a monitoring application. In preferred embodiments, this takes place automatically, either when the computer is booted or when a target application is started. The monitoring application checks all open windows forms and URL windows 102 and compares 104 the captions of windows forms and/or the URL addresses of URL windows to a target alphanumeric string. If there is no match, then the monitoring application waits for a specified amount of time 106, which in preferred embodiments is 500 ms, and then checks again. If the target string is successfully matched by a target window, the monitoring application then determines of the target window is active 108. If not, then any prompting window attached to the target window is removed 110, and the monitoring application waits 106 and then repeats the check.

If an active target window is found, the monitoring application determines its size and placement 112 and then displays a prompting window 114. When possible, the prompting window will be seemingly attached to the target window, with one edge of the prompting window aligned with an edge of the target windows. The prompting window will extend outside of the target window if there is sufficient space, or it will overlap the target window if important information is not thereby obscured. If attachment is not possible, then a detached prompting window will be displayed, typically at the top of the screen. At this point, one or more controls included in the prompting window are presented and available for activation 116, and the monitoring application resumes its window-checking cycle.

When a control on the prompting window is selected 118, a second, coordinating application is activated 120, and the monitoring application proceeds to obtain relevant information from the target application 122 and transfer it to the coordinating application 124. In some embodiments, information is obtained from the target application by reading a file intentionally stored by the target application in a well defined location use by other applications. In some of these embodiments the format of the file is either XML and/or ASCII text. In other preferred embodiments the information is obtained from the target application through an interprocess communication protocol, such as a COM protocol. In still other embodiments, a so-called "screen-scraping" approach is applied wherein html tags from the target desktop application window are reviewed so as to find the controls in the target window that contained the desired information.

In preferred embodiments, the prompting window can contain a plurality of controls, selection of which can cause activation of different coordinating applications, activation of the same coordinating applications but in different modes, and/or transfer of different information from the target application to the coordinating application.

Figure 2A:
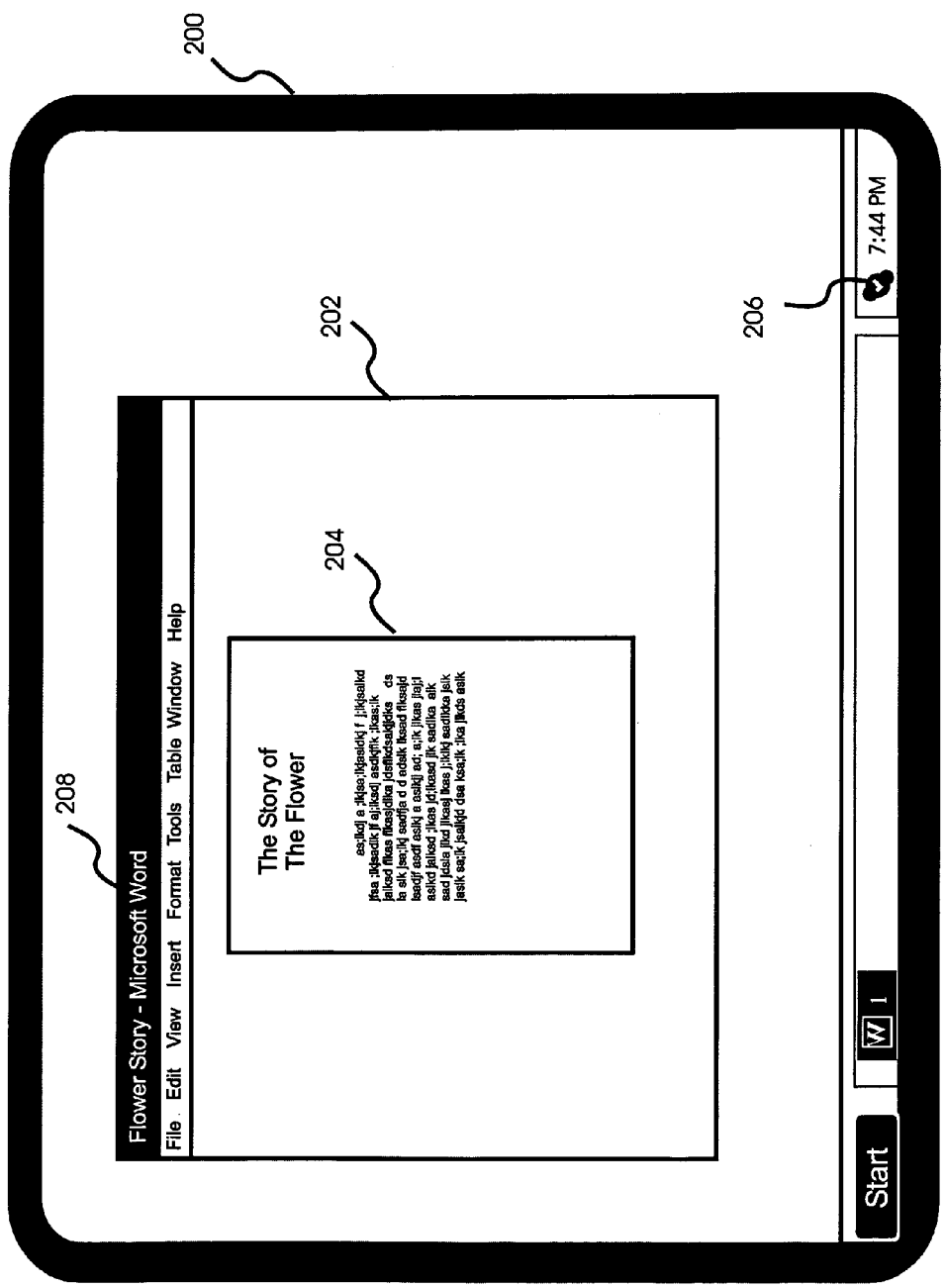
FIG. 2A is an illustration of a computer display showing an active word processing windows form.
Figure 2C:
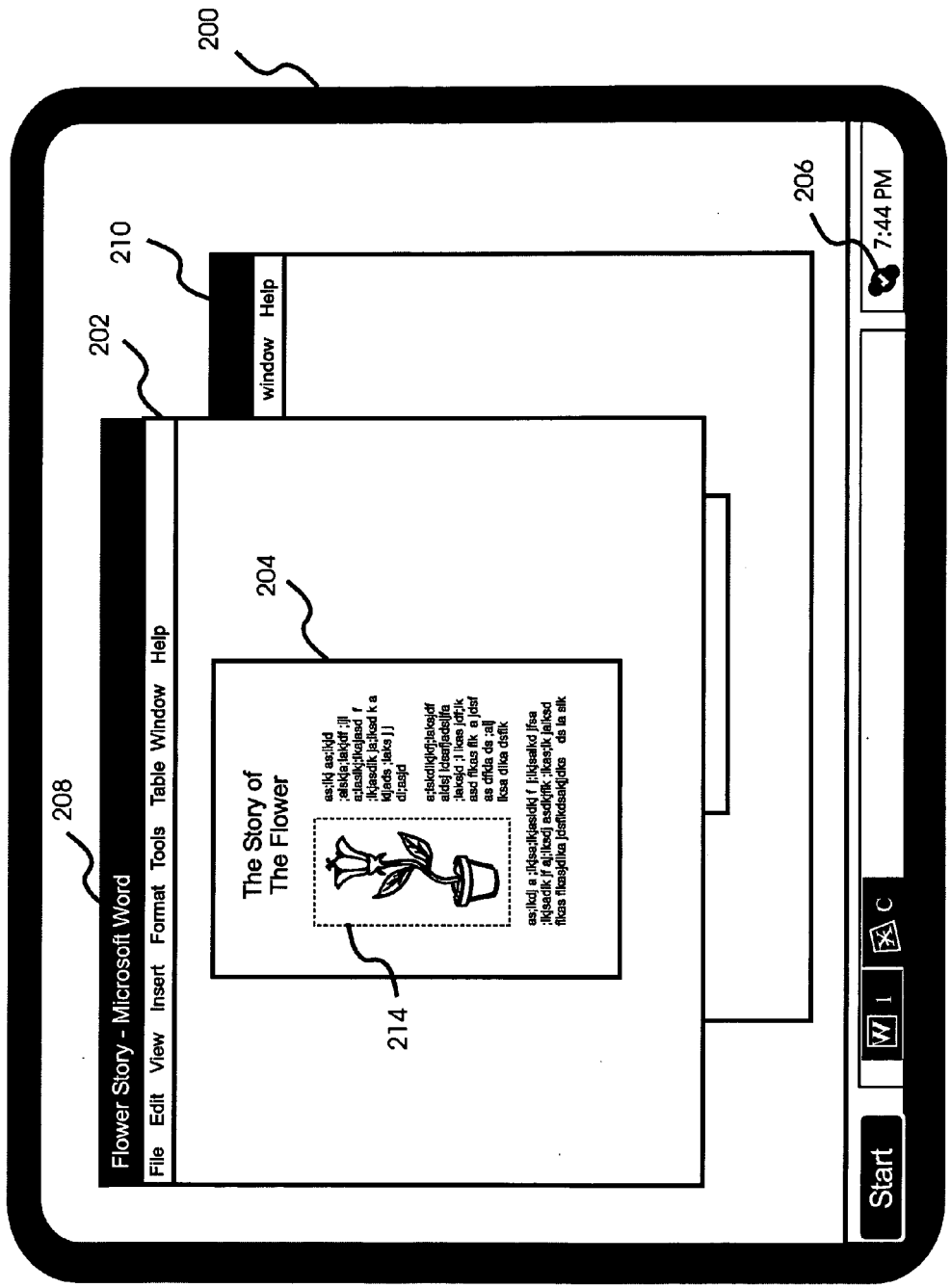
FIG. 2C is an illustration of the computer display of FIG. 2A with the word processing windows form activated and a graphical illustration from the graphical illustration windows form automatically transferred thereto.

An example of the method illustrated in FIG. 1 is presented in FIG. 2A, FIG. 2B, and FIG. 2C. FIG. 2A illustrates a computer display 200 on which a windows form 202 from a document processing application is presented. A document 204 in preparation is shown in the windows form 202. The monitoring application has already been activated, as can be seen from the appearance of a small icon 206 in the task bar at the bottom of the screen 200. The monitoring application has compared the caption 208 of the windows form 202, and found that it does not match the target text.

FIG. 2B illustrates the computer display 200 of FIG. 2A with a second windows form 210 presented. The second windows form 210 is generated by a graphical illustration application, and is displaying a completed illustration 212 in the window 210. The monitoring application has successfully identified the second windows form 210 as a target windows form by matching the caption 214 of the target windows form 210 it to a target alphanumeric string. Since the target window 210 is active, the monitoring application has displayed a prompting window 216 in a location that causes it to appear to be attached to the target windows form 210. Since the target windows form 210 does not occupy the entire display 200, the monitoring application has attached the prompting window 216 to the target windows form 210 such that it extends outward from the target window 210. A cursor 218 is positioned over a control 220 on the prompting window 216 and is ready to select the control 220. In FIG. 2, the prompting window 216 is shown as being attached to the right side of the target window 210. In preferred embodiments, the prompting window 216 can also be attached to the top, bottom, or left side of the target window 210, depending on the placement of the target window 210 on the computer display 200.

FIG. 2C illustrates the computer display of FIG. 2A and FIG. 2B as it appears after selection of the control 220 on the prompting window 216. The first windows form 202 has been activated, and the prompting window has been removed since the target window 210 is no longer active. In addition, the monitoring application has extracted the displayed graphical illustration 214 from the target form 210 and has automatically inserted it into the document 204 being prepared in the first windows form 202.

Figure 3A:
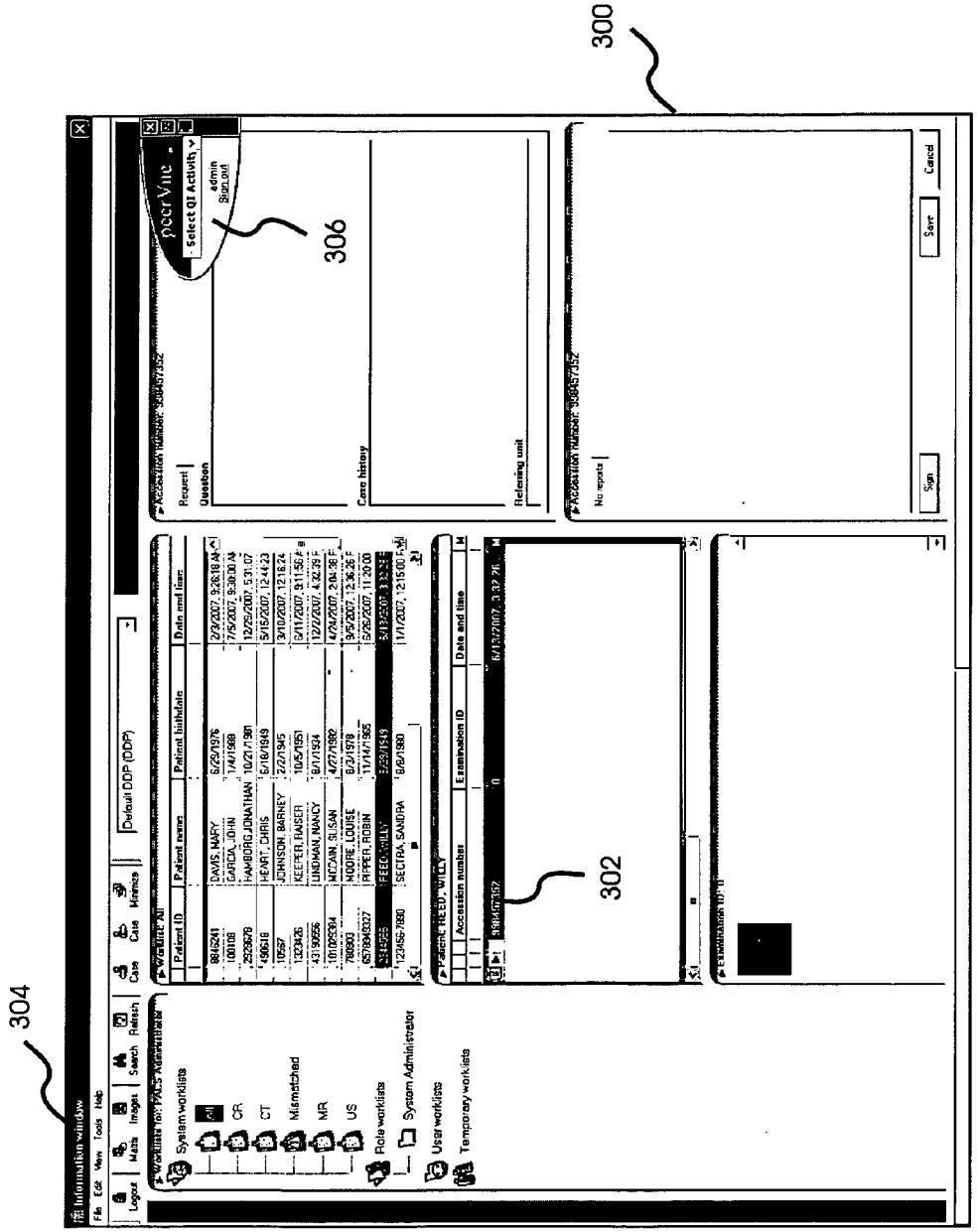
FIG. 3A is an illustration of an active windows form generated by a medical image processing application, with a prompting window attached to and overlapping the windows form.
Figure 3C:
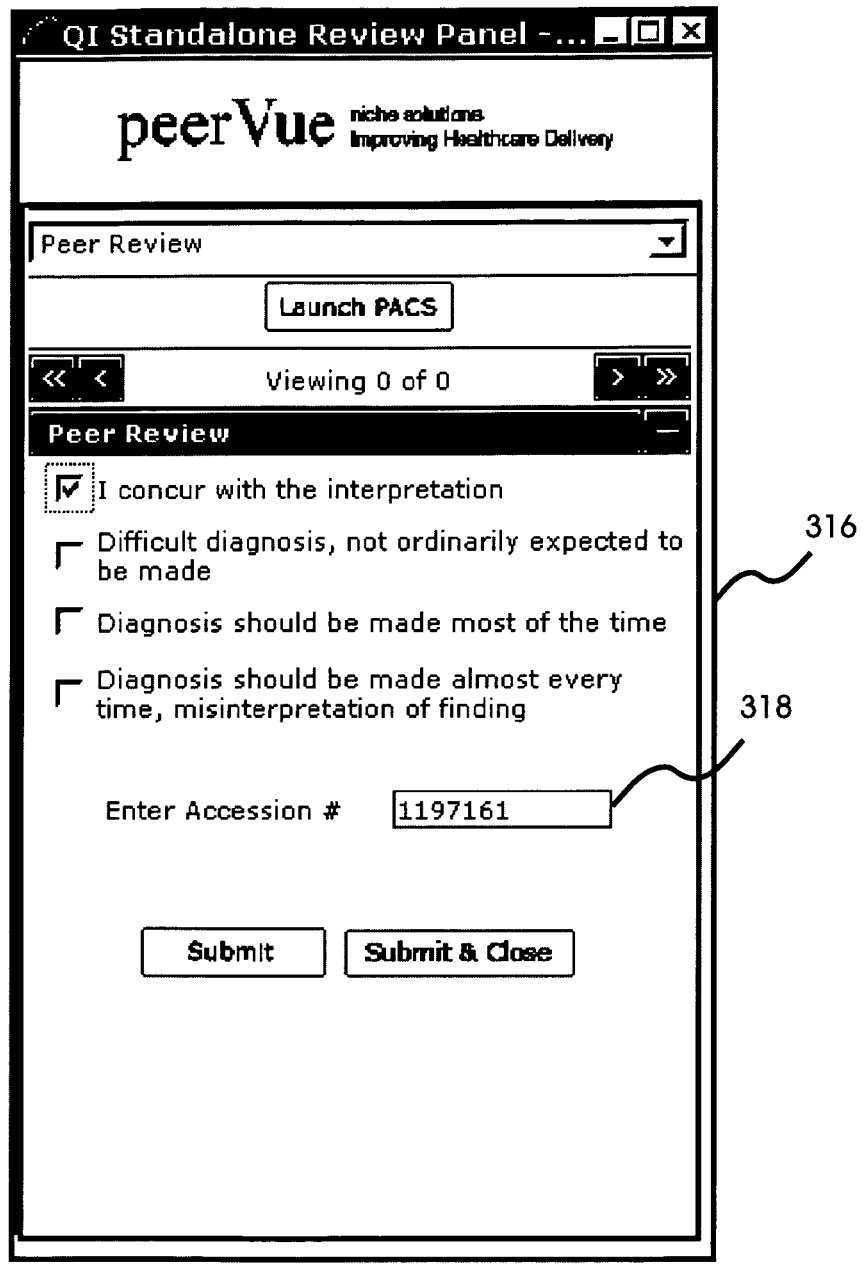
FIG. 3C is a windows form generated by software that facilitates peer review of medical image interpretations, the windows form being automatically populated with the accession number of the currently selected imaging study from the medical image processing software.

FIG. 3A, FIG. 3B, and FIG. 3C illustrate application of the method to software that is used to view medical imaging results. FIG. 3A illustrates a windows form 300 generated by a medical test result viewing application. A list of medical imaging results is presented with associated information, and one of the imaging studies 302 has been selected. The caption 304 of the form 300 has been matched by the monitoring application, and a prompting window 306 has been attached to the form 300. Although the windows form 300 fills the display 200, there is space within the form 300 where the prompting window 306, so the prompting window 306 has been displayed as attached to an edge of the form 300 and extending inward on top of the form 300.

FIG. 3B presents an enlarged view of the prompting window 306. The prompting window 306 includes a drop-down list 308 of selectable controls, as well as additional controls that can be used to close 310, minimize 312, and detach 314 the prompting window 306. A cursor 218 is positioned over the drop-down list 308 and is ready to select one of the controls.

FIG. 3C illustrates a windows form 316 generated by a secondary medical test result processing application, which in this example is used to facilitate the reporting of peer reviews of radiologist interpretations of medical imaging results. The peer review windows form 316 has been automatically activated upon selection of a control on the prompting window 306, and the accession number of the selected imaging study 302 has been automatically obtained from the medical test result viewing application windows form 300 and inserted into an appropriate location 318 on the peer review windows form 316.

What is claimed is:

1. A computer software system having a set of instructions for controlling a computer to facilitate interaction between two software applications operable on the computer, the set of instructions stored on non-transitory computer-readable media that are executed by the computer to carry out a method comprising:

monitoring the computer to identify an active target window of a target application from among all currently open windows, wherein at least some of the windows currently open on the computer are associated with an alphanumeric identifier in a form of a caption or an address, and wherein monitoring the computer comprises identifying the active target window at least partly by matching some or all of its caption or address with a target alphanumeric string;

in response to the identification of an active target window, displaying a prompting window in a visible location cooperative with the identified active target window, the prompting window including one or more selectable controls; and in response to selection of one of the one or more controls:
activating a coordinating application associated with the selected control;
obtaining information from the target application of the identified active target window, wherein the information existed in the target application at the time at which the one or more controls were selected;
providing the information to the coordinating application; and
inactivating the target application,
wherein monitoring the computer comprises determining a size and placement of the active target window, and wherein displaying the prompting window comprises displaying the prompting window in a manner dependent upon the size and placement of the active target window by displaying the prompting window so as to have an edge aligned with an edge of the active target window and to extend outward from the active target window in an instance in which the active target window does not occupy the entire display or to otherwise overlap the active target window.

2. The computer software system of claim 1, wherein the alphanumeric identifier of each open window is compared at regular intervals of time with the target alphanumeric string.

3. The computer software system of claim 1, wherein the caption is displayed as part of the window.

4. The computer software system of claim 1, wherein the identified target window is a URL window displayed by an HTML browsing application and the alphanumeric identifier associated with the target URL window is a URL address.

5. The computer software system of claim 1, wherein the one or more controls includes at least two controls, each of which corresponding to a different software application, such that the application corresponding to the selected one of the controls is activated to become the coordinating application.

6. The computer software system of claim 1, wherein the one or more controls includes at least two controls, each of which corresponding to a different, alternative operational mode of the same software application, such that the application is activated as the coordinating application in the operational mode of the coordinating application corresponding to the selected one of the controls.

7. The computer software system of claim 1, wherein the prompting window can be displayed with an edge substantially coincident with an edge of the target window, so as to cause the prompting window to appear to be attached to the target window.

8. The computer software system of claim 1, wherein the information is extracted from a file created by the target application.

9. The computer software system of claim 8, wherein the format of the file is one of: XML and ASCII text.

10. The computer software system of claim 1, wherein the information is obtained from the target application through an interprocess communication protocol.

11. The computer software system of claim 10, wherein the interprocess communication protocol is a COM (Component Object Module) protocol.

12. The computer software system of claim 1, wherein the information is obtained from the target application by extracting it from the target window.

13. The computer software system of claim 1, wherein said monitoring is initiated in response to booting up the computer.

14. The computer software system of claim 1, wherein, in response to selection of one of the one or more controls, the method further comprises removing the prompting window.

15. The computer software system of claim 1, wherein obtaining information from the target application of the identified active target window comprises obtaining information from the target application by screen scraping.

16. A computer software system having a set of instructions for controlling a computer to facilitate interaction between a medical test result viewing application and a secondary medical test result processing application, the set of instructions stored on non-transitory computer-readable media that are executed by the computer to carry out a method comprising:

continuously monitoring the computer to identify an active target window of the medical test result viewing application from among windows currently displayed by the computer, wherein at least some of the windows currently open on the computer are associated with an alphanumeric identifier in a form of a caption or an address, and wherein monitoring the computer comprises identifying the active target window at least partly by matching some or all of its caption or address with a target alphanumeric string;

in response to the identification of the active target window, displaying a prompting window in a visible location cooperative with the identified active target window, the prompting window including at least one selectable control; and in response to selection of the at least one control:

activating the secondary medical test result processing application associated with the selected at least one control;

obtaining information pertaining to a selected test result from the medical test result viewing application, wherein the information existed in the medical test result viewing application at the time at which the at least one control was selected; and providing the information to the secondary medical test result processing application; and inactivating the medical test result viewing application, wherein monitoring the computer comprises determining a size and placement of the active target window, and wherein displaying the prompting window comprises displaying the prompting window in a manner dependent upon the size and placement of the active target window by displaying the prompting window so as to have an edge aligned with an edge of the active target window and to extend outward from the active target window in an instance in which the active target window does not occupy the entire display or to otherwise overlap the active target window.

17. The computer software system of claim 16, wherein the prompting window can be displayed with an edge substantially coincident with an edge of the target window, so as to cause the prompting window to appear to be attached to the target window.

\* \* \* \* \*